(12) United States Patent
Lee et al.

(10) Patent No.: US 10,716,479 B2
(45) Date of Patent: Jul. 21, 2020

(54) SIGNAL SYNCHRONIZATION DEVICE, AS WELL AS STETHOSCOPE, AUSCULTATION INFORMATION OUTPUT SYSTEM AND SYMPTOM DIAGNOSIS SYSTEM CAPABLE OF SIGNAL SYNCHRONIZATION

(71) Applicant: National Cheng Kung University, Tainan (TW)

(72) Inventors: Shuenn-Yuh Lee, Tainan (TW); Ju-Yi Chen, Tainan (TW); Yu-Jin Lin, Changhua County (TW); Peng-Wei Huang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 304 days.

(21) Appl. No.: 15/826,648

(22) Filed: Nov. 29, 2017

(65) Prior Publication Data
US 2019/0150756 A1  May 23, 2019

(30) Foreign Application Priority Data
Nov. 17, 2017  (TW) .............................. 106140002 A

(51) Int. Cl.
| | |
|---|---|
| A61B 5/0205 | (2006.01) |
| A61B 5/04 | (2006.01) |
| A61B 7/04 | (2006.01) |
| A61B 5/044 | (2006.01) |
| A61B 5/00 | (2006.01) |

(Continued)

(52) U.S. Cl.
CPC .......... *A61B 5/0205* (2013.01); *A61B 5/0006* (2013.01); *A61B 5/0024* (2013.01); *A61B 5/0402* (2013.01); *A61B 5/044* (2013.01); *A61B 5/04012* (2013.01); *A61B 5/7207* (2013.01); *A61B 7/04* (2013.01); *A61B 5/0022* (2013.01); *A61B 5/04525* (2013.01); *A61B 5/725* (2013.01); *A61B 2560/0223* (2013.01)

(58) Field of Classification Search
CPC ... A61B 5/0205; A61B 5/7207; A61B 5/0402; A61B 5/0006; A61B 5/0024; A61B 5/044; A61B 7/04; A61B 5/04012; A61B 5/725; A61B 5/0022; A61B 2560/0223; A61B 5/04525
See application file for complete search history.

(56) References Cited

U.S. PATENT DOCUMENTS

| | | | | |
|---|---|---|---|---|
| 5,337,752 A | * | 8/1994 | Reeves | ................ A61B 5/0017 600/513 |
| 9,008,762 B2 | * | 4/2015 | Brockway | ................ A61B 7/00 600/515 |
| 9,521,956 B2 | * | 12/2016 | Bedingham | ............... A61B 7/04 |

* cited by examiner

*Primary Examiner* — Mark Bockelman
(74) *Attorney, Agent, or Firm* — Chun-Ming Shih; Lanway IPR Services

(57) ABSTRACT

The invention provides a signal synchronization device, which obtains electrocardiographic, heart sound signal calibration factors by performing time domain and frequency domain transformations for an electrocardiographic signal and a heart sound signal, and thereby performs calibration for the electrocardiographic signal and the heart sound signal to synchronize the electrocardiographic signal and the heart sound signal in time domain, such that a diagnosis rate for cardiovascular disease is increased. Moreover, the invention further provides a stethoscope with signal synchronization processing, an auscultation information output system and a symptom diagnosis system capable of signal synchronization.

8 Claims, 11 Drawing Sheets

(51) Int. Cl.
*A61B 5/0402* (2006.01)
*A61B 5/0452* (2006.01)

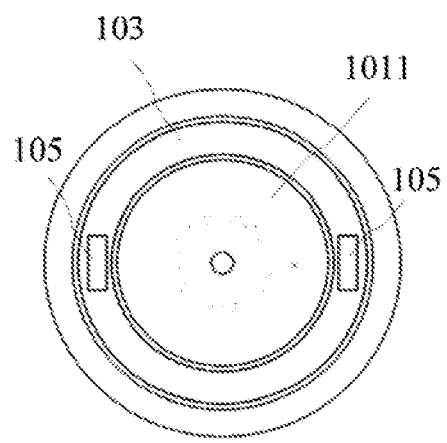
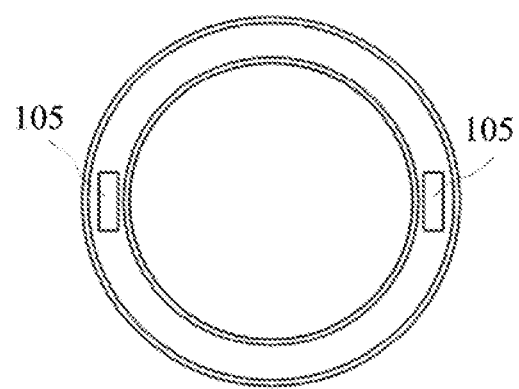
Figure 2C
Figure 2D

SIGNAL SYNCHRONIZATION DEVICE, AS WELL AS STETHOSCOPE, AUSCULTATION INFORMATION OUTPUT SYSTEM AND SYMPTOM DIAGNOSIS SYSTEM CAPABLE OF SIGNAL SYNCHRONIZATION

CROSS-REFERENCE TO RELATED APPLICATIONS

This application claims the priority of Republic of China Patent Application No. 106140002 filed on Nov. 17, 2017, in the State Intellectual Property Office of the R.O.C., the disclosure of which is incorporated herein by reference.

BACKGROUND OF THE INVENTION

Field of the Invention

The invention relates to a signal processing technique, and more specifically to a signal synchronization device with respect to electrocardiographic signals and heart sound signals, as well as a stethoscope, an auscultation information output system and a symptom diagnosis system capable of signal synchronization.

Descriptions of the Related Art

Electrocardiographic signals and heart sound signals are physiological signals generated when cardiac muscles work. Analyzes of electrocardiographic and heart sound signals are two important means and standards for heart diseases.

Wherein, electrocardio shows an electrical physiological activity of a hear on a body surface and is a foundation for diagnosis of clinical heart disease, while a heart sound is a response for a mechanical motion of a heart and a cardiovascular system, wherein physiological information and pathological information of various portions of the heart and interaction therebetween are included. In clinical diagnosis of a heart, an electrocardiographic signal may be used to detect common heart diseases rapidly and easily, especially for myocardial infarction and arrhythmias. However, lesions of some heart tissues would not be reflected in the electrocardiographic signal directly, but can appear in a heart sound signal.

However, a separate condition of dynamic electrocardiogram and cardiophonogram exists for current clinic. Electrocardiographic and heart sound signal data cannot be acquired synchronously for synchronous analysis, so that certain difficulties exist in current early diagnosis of cardiovascular diseases, researching for pathogenesis of cardiovascular disease and researching for prevention of cardiovascular disease.

In view of this, it is the technical subject the invention to be solved with respect to how to acquire electrocardiographic signals and heart sound signals, as well as perform synchronization of both signals for increasing diagnosis rate of cardiovascular disease accordingly.

SUMMARY OF THE INVENTION

In view of the shortages of prior arts mentioned above, the major objective of the invention is to provide a signal synchronization device, as well as a stethoscope, an auscultation information output system and a symptom diagnosis system capable of signal synchronization, which may provide synchronization for an electrocardiographic signal and a heart sound signal such that both signals are synchronous in time domain.

Another objective of the invention is to provide a signal synchronization device, as well as a stethoscope, an auscultation information output system and a symptom diagnosis system capable of signal synchronization, which may increase a diagnosis rate for a cardiovascular disease effectively.

For the objects said above and for other objects, the invention provides a signal synchronization device used to perform synchronous calibration for an electrocardiographic signal and a heart sound signal, including: a signal receiving module for receiving the electrocardiographic signal and the heart sound signal separately to generate a first electrocardiographic time domain information and a first heart sound time domain information separately, the first electrocardiographic time domain information comprising a first electrocardio generation time point of the electrocardiographic signal, the first heart sound time domain information comprising a first heart sound generation time point of the heart sound signal; a synchronization factor generation module for receiving the electrocardiographic signal and the heart sound signal synchronously to generate a mixed time domain information, and performing time domain and frequency domain transformations for the mixed time domain information to obtain a second electrocardiographic time domain information representing the electrocardiographic signal in the mixed time domain information, the second electrocardiographic time domain information comprising a second electrocardio generation time point of the electrocardiographic signal, and to obtain a second heart sound time domain information representing the heart sound signal in the mixed time domain information, the second heart sound time domain information comprising a second heart sound generation time point of the heart sound signal, and allowing the second electrocardio generation time point and the second heart sound generation time point to be synchronous in time domain for using the second heart sound time domain information as an electrocardiographic signal calibration factor, and using the second heart sound time domain information as a heart sound signal calibration factor; and a synchronization module used to calibrate the electrocardiographic signal and the heart sound signal received by the signal receiving module at least once according to the electrocardiographic signal synchronization factor and the heart sound signal synchronization factor separately for the first electrocardio generation time point and the second electrocardio generation time point to be consistent, and for the first heart sound generation time point and the second heart sound generation time point to be consistent, such that the electrocardiographic signal and the heart sound signal received by the signal receiving module are synchronous in time domain.

Optionally, for the signal synchronization device said above, wherein the synchronization factor generation module performs a time domain to frequency domain transformation for the mixed time domain information to generate a mixed frequency domain information, followed by acquiring a main frequency characteristic in the mixed frequency domain information, and defining a heart sound frequency domain information representing the heart sound signal and defining an electrocardiographic frequency domain information representing the electrocardiographic signal from the mixed frequency domain information according to the main frequency characteristic, followed by performing a frequency domain to time domain transformation for the mixed frequency domain information to generate the mixed time domain information, in order to define the second heart sound time domain information in the mixed time domain signal by the heart sound frequency domain information and define the second electrocardiographic time domain information in the mixed time domain signal by the electrocardiographic frequency domain information.

The invention further provides a stethoscope for auscultating a user, including: a pickup member for collecting the heart sound signal of the user; a sound guiding pipe for conducting the heart sound signal; a slave member sheathing the pickup member for contacting the user due to a motion of the pickup member; a heart sound transducer arranged on the sound guiding pipe, the heart sound transducer having a heart sound transduction portion, which is oriented to the pickup member for acquiring the heart sound signal; an electrocardio transducer arranged on the slave member, the electrocardio transducer having an electrocardio transduction portion, which is exposed to a portion of the slave member contacting the user for acquiring the electrocardiographic signal; and the signal synchronization device said above performing time domain synchronization for the heart sound signal acquired by the heart sound transducer and the electrocardiographic signal acquired by the electrocardio transducer.

Optionally, for the stethoscope said above, further including: a wireless transceiver module outputting the heart sound signal and the electrocardiographic signal, which are synchronous in time domain, wirelessly.

Optionally, for the stethoscope said above, wherein the wireless transceiver module can be a Bluetooth transceiver module, a Wi-Fi transceiver module, a ZigBee transceiver module or any customized wireless transceiver module.

The invention further provides an auscultation information output system, including: the stethoscope; a graphic processing module for patterning the heart sound signal and the electrocardiographic signal synchronized by the stethoscope in time domain to generate an electrocardio graphic information and a heart sound graphic information; and a display module for displaying the electrocardio graphic information and the heart sound graphic information.

The invention further provides a symptom diagnosis system, including: a database for storing a heart sound symptom information and an electrocardiographic symptom information; the stethoscope said above; an analysis module for analyzing the heart sound signal and the electrocardiographic signal synchronized by the stethoscope in time domain to obtain a heart sound characteristic included in the heart sound signal, and obtain an electrocardiographic characteristic included in the electrocardiographic signal; and a system diagnosis module, which outputs a heart sound system diagnosis result comprising the heart sound symptom information as the heart sound characteristic and the heart sound symptom information are matched; outputs an electrocardiographic system diagnosis result comprising the electrocardiographic symptom information as the electrocardiographic characteristic and the electrocardiographic symptom information are matched.

Optionally, for the symptom diagnosis system said above, further including: an expert diagnosis module, which diagnoses the heart sound signal and outputs a heart sound expert diagnosis result, and diagnoses the electrocardiographic signal and outputs an electrocardiographic expert diagnosis result; and a symptom update module, which corrects/updates the heart sound symptom information of the database according to the heart sound expert diagnosis result as the heart sound system diagnosis result and the heart sound expert diagnosis result are mismatched; corrects/updates the electrocardiographic symptom information of the database according to the electrocardiographic expert diagnosis result as the electrocardiographic system diagnosis result and the electrocardiographic expert diagnosis result are mismatched.

Optionally, for the symptom diagnosis system said above, further including: the stethoscope said above capable of providing a stethoscope binding instruction and a stethoscope unbinding instruction; a client terminal, which provides a client terminal binding instruction and client terminal unbinding instruction; and a cloud platform, which can create a binding relationship of the stethoscope and the client terminal only when the stethoscope binding instruction and the client terminal binding instruction are received simultaneously so that the client terminal can receive the heart sound signal and the electrocardiographic signal synchronized by the stethoscope in time domain, or relieve the binding relationship of the stethoscope and the client terminal only when the stethoscope unbinding instruction and the client terminal unbinding instruction are received simultaneously.

Compared to the conventional technology, the signal synchronization device provided in the invention generates a mixed time domain information by receiving an electrocardiographic signal and a heart sound signal synchronously, and performs time domain and frequency domain transformations for the mixed time domain information to obtain an electrocardiographic signal calibration factor and a heart sound signal calibration factor separately, in order to perform calibrations for the electrocardiographic signal and the heart sound signal according to the electrocardiographic signal calibration factor and the heart sound signal calibration factor separately, so that a technical effect of synchronizing the output electrocardiographic and heart sound signals in time domain is realized. Moreover, the invention may increase the diagnosis rate for a cardiovascular disease effectively by applying the signal synchronization device to the stethoscope, the auscultation information output system and the symptom diagnosis system.

BRIEF DESCRIPTION OF THE DRAWINGS

The above and other aspects, features and other advantages of the present invention will be more clearly understood from the following detailed description taken in conjunction with the accompanying drawings, in which:

FIGS. 2B-2G are schematic views showing different examples of the stethoscope shown in FIG. 2A;

DETAILED DESCRIPTION OF THE PREFERRED EMBODIMENT

Figure 1:
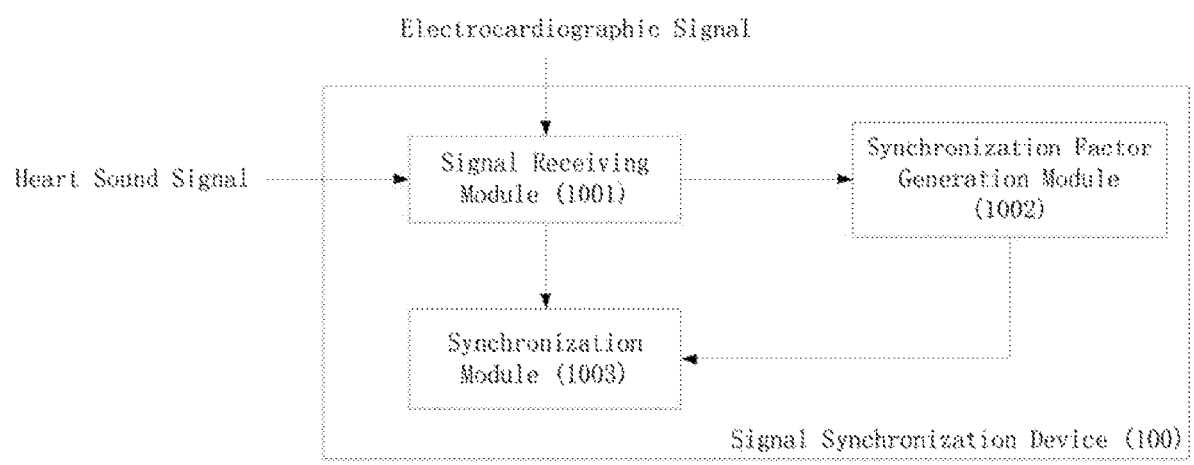
FIG. 1 is a schematic view showing a basic framework of a signal synchronization device in a first implementation of the invention.

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

FIG. 1 is a schematic view showing a basic architecture of a signal synchronization device 100 of the invention. As shown in FIG. 1, the signal synchronization device 100 of the invention is used to perform synchronous calibration for an electrocardiographic signal and a heart sound signal to synchronize both signals in time domain in order for increasing a diagnosis rate of cardiovascular diseases accordingly. As shown in the figure, the signal synchronization device 100 mainly includes a signal receiving module 1001, a synchronization factor generation module 1002 and a synchronization module 1003.

The signal receiving module 1001 is used for receiving the electrocardiographic signal and the heart sound signal separately to generate a first electrocardiographic time domain information and a first heart sound time domain information separately, and the first electrocardiographic time domain information comprises a first electrocardio generation time point of the electrocardiographic signal therein, while the first heart sound time domain information comprises a first heart sound generation time point of the heart sound signal therein. In an example, the signal receiving module 1001 may receive the electrocardiographic signal and the heart sound signal by a signal acquisition module (not shown) arranged in the signal synchronization device 100. However, the signal receiving module 1001 is not limited thereto, but may also receive the electrocardiographic signal and the heart sound signal through an external electronic equipment in other examples.

The synchronization factor generation module 1002 is used for receiving the electrocardiographic signal and the heart sound signal synchronously to generate a mixed time domain information, and performing time domain and frequency domain transformations for the generated mixed time domain information to obtain a second electrocardiographic time domain information representing the electrocardiographic signal in the mixed time domain information, wherein the second electrocardiographic time domain information comprises a second electrocardio generation time point of the electrocardiographic signal, while obtaining a second heart sound time domain information representing the heart sound signal from the mixed time domain information, wherein the second heart sound time domain information comprises a second heart sound generation time point of the heart sound signal, and allows the second electrocardio generation time point and the second heart sound generation time point to be synchronous in time domain for using the second heart sound time domain information as an electrocardiographic signal calibration factor, and using the second heart sound time domain information as a heart sound signal calibration factor.

In an example, the synchronization factor generation module 1002 receives the electrocardiographic signal and the heart sound signal of the signal receiving module 1001 simultaneously at first to generate a mixed time domain information, and performs time domain and frequency domain transformations for the mixed time domain information to generate a mixed frequency domain information, followed by acquiring main frequency characteristics (i.e., main frequencies of the signals) in the mixed frequency domain information. The main frequency of the electrocardiographic signal and that of the heart sound signal are not the same (generally, the frequency of an electrocardiographic signal of a human body is below 50 Hz, while that of a heart sound signal is between 50 Hz and 120 Hz), so that a heart sound frequency domain information representing the heart sound signal and an electrocardiographic frequency domain information representing the electrocardiographic signal may be defined from the mixed frequency domain information separately according to a frequency difference of the acquired main frequency characteristics, i.e., the electrocardiographic signal and the heart sound signal are separated from the mixed frequency domain information. After that, a recovery transformation from frequency domain to time domain is performed for the mixed frequency domain information to restore the mixed frequency domain information to the mixed time domain information. Subsequently, a second heart sound time domain information is defined from the restored mixed time domain information by the heart sound frequency domain information, and a second electrocardiographic time domain information is defined from the restored mixed time domain information by the electrocardiographic frequency domain information, wherein the second heart sound generation time point of the heart sound signal is included in the second heart sound time domain information, while the second electrocardio generation time point of the electrocardiographic signal is included in the second electrocardiographic time domain information, such that actual signal time points of heart sound and electrocardio are marked thereby. Furthermore, the second electrocardio generation time point and the second heart sound generation time point are synchronous in time domain by way of, for example, adjustment of time axis to use the second electrocardiographic time domain information as the electrocardiographic signal calibration factor and use the second heart sound time domain information as the heart sound signal calibration factor.

The synchronization module 1003 is used to perform calibration at least once for the electrocardiographic signal and the heart sound signal received by the signal receiving module 1001 according to the electrocardiographic signal synchronization factor and the heart sound signal synchronization factor generated by the synchronization factor generation module 1002 separately, such that the first electrocardio generation time point and the second electrocardio generation time point in the electrocardiographic signal are consistent, and the first heart sound generation time point and the second heart sound generation time point in the heart sound signal are consistent, in order for the electrocardiographic signal and the heart sound signal received by the signal receiving module 1001 to be synchronous in time domain.

Specifically, the synchronization module 1003 corrects a delay time of the electrocardiographic signal and the heart sound signal received by the signal receiving module 1001 according to the electrocardiographic signal synchronization factor and the heart sound signal synchronization factor separately. Since the second electrocardio generation time point and the second heart sound signal have been synchronized in time domain for the second electrocardiographic time domain information and the second heart sound time domain information to be synchronized, the second electrocardiographic time domain information and the second heart sound time domain information are used as the electrocardiographic signal calibration factor and the heart sound signal calibration factor separately for calibration, followed by being capable of obtaining the electrocardiographic signal and the heart sound signal which are synchronous in time domain.

Furthermore, the synchronization module 1003 may perform fine tuning for time axes of the electrocardiographic signal and the heart sound signal at least once to improve synchronization effect of the electrocardiographic signal and the heart sound signal thereby. Specifically, after the synchronization module 1003 has performed a first calibration for the electrocardiographic signal and the heart sound signal separately, the synchronization factor generation module 1002 may be allowed to perform an identical operation processing again for the electrocardiographic signal and the heart sound signal output by the synchronization module 1003 after the first calibration, i.e., the electrocardiographic signal and the heart sound signal after the first calibration are received synchronously, to generate the mixed time domain information, and to perform time domain and frequency domain transformations for the mixed time domain information for obtaining the second electrocardiographic time domain information representing the electrocardiographic signal in the mixed time domain information, the second electrocardiographic time domain information comprising the second electrocardio generation time point of the electrocardiographic signal therein, and further obtaining the second heart sound time domain information representing the heart sound signal in the mixed time domain information, the second heart sound time domain information comprising the second heart sound generation time point of the second heart sound signal. Subsequently, whether or not the second electrocardio generation time point and the second heart sound generation time point are synchronous in time domain is determined. In case of not being synchronous, a secondary fine tuning of time axis is performed for the second electrocardio generation time point and the second heart sound generation time point to be synchronous in time domain, while the second electrocardiographic time domain information is sued as the electrocardiographic signal calibration factor and the second heart sound time domain information is used as the heart sound signal calibration factor for the synchronization module 1003 to perform a second calibration for the electrocardiographic signal and the heart sound signal after the first calibration accordingly. Through such recurring repetitive operations of the synchronization factor generation module 1002 and the synchronization module 1003, a processing effect that the electrocardiographic signal and the heart sound signal received by the signal receiving module 1001 are synchronous in time domain is achieved.

Figure 2A:
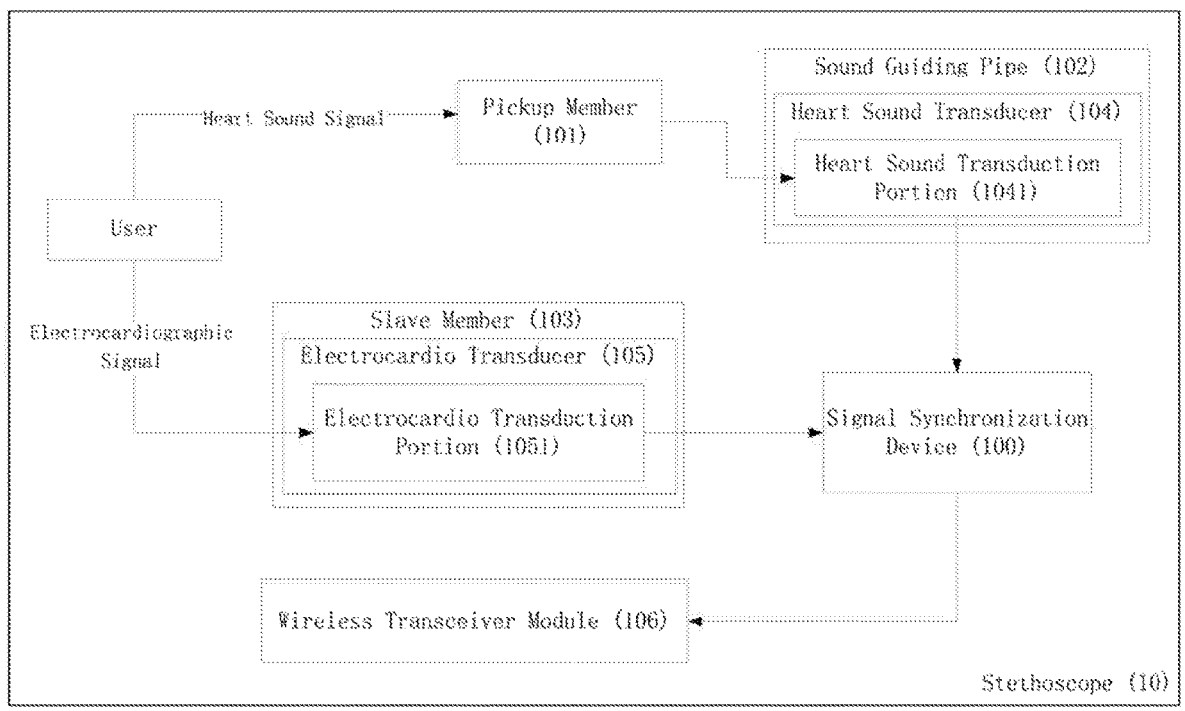
FIG. 2A is a schematic view showing a basic framework of a stethoscope in a second implementation of the invention.

FIG. 2A is a schematic view showing a basic framework of a stethoscope in a second implementation of the invention. A stethoscope 10 is used for performing an auscultation operation of a user, and has a processing capability of signal synchronization. As shown in the figure, the stethoscope 10 mainly includes a pickup member 101, a sound guiding pipe 102, a slave member 103, a heart sound transducer 104, an electrocardio transducer 105 and the signal synchronization device 100 mentioned in the first implementation.

Figure 2B:
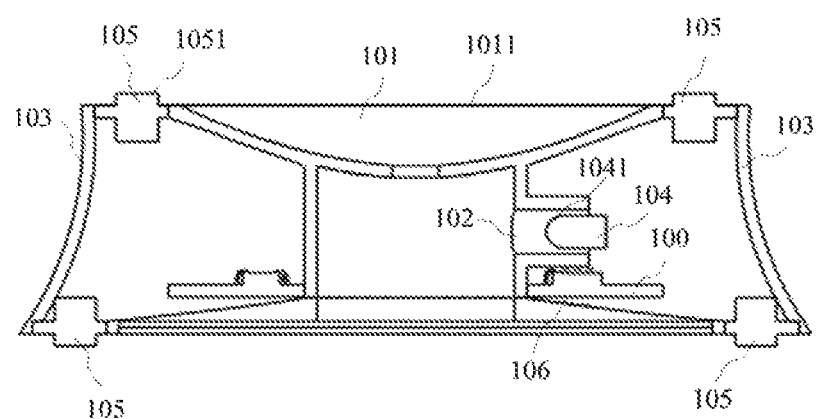

The pickup member 101 is used to acquire a heart sound signal of the user. As shown in FIG. 2B, a surface of the pickup member 101 is covered with a layer of pickup film 1011, which may not only avoid dust from entering, but also get adhered onto a body surface of the user well, in order to acquire the heart sound signal.

The sound guiding pipe 102 is used to conduct the heart sound signal acquired by the pickup member 101.

Refer to FIGS. 2B and 2C in conjunction, the slave member 103 sheathes the pickup member 101. The slave member 103 may be coplanar with the pickup film fundamentally to contact the body surface of the user due to a motion of the pickup member 101.

As shown in FIG. 2B, the heart sound transducer 104 is arranged on the sound guiding pipe 102 and has a heart sound transduction portion 1041, wherein the heart sound transduction portion 1041 is oriented to the pickup member 101 for acquiring the heart sound signal of the user through the pickup member 101. In a preferred example, the stethoscope 10 may also has a built-in speaker to play the acquired heart sound signal directly.

Refer to FIGS. 2A to 2D in conjunction, the electrocardio transducer 105 is arranged on the slave member 103 and has an electrocardio transduction portion 1051. As shown in FIG. 2B, the electrocardio transduction portion 1051 contacts a portion of the user for acquiring an electrocardiographic signal of the user through exposure to the slave member 103. In an example, the electrocardio transduction portion 1051 is multiple electrodes, which, for example, are distributed around the pickup member 101 uniformly, for acquiring biological electrical signals from a human body of the user.

The signal synchronization device 100 is used to receive the heart sound signal acquired by the heart sound transducer 104 and the electrocardiographic signal acquired by the electrocardio transducer 105 separately, and perform synchronization for the electrocardiographic signal and the heart sound signal in time domain. Since a structure configuration and a signal synchronization means of the signal synchronization device 100 have been mentioned in detail when describing the signal synchronization device 100 shown in FIG. 1 above, there is no redundant description here.

Figure 2E:
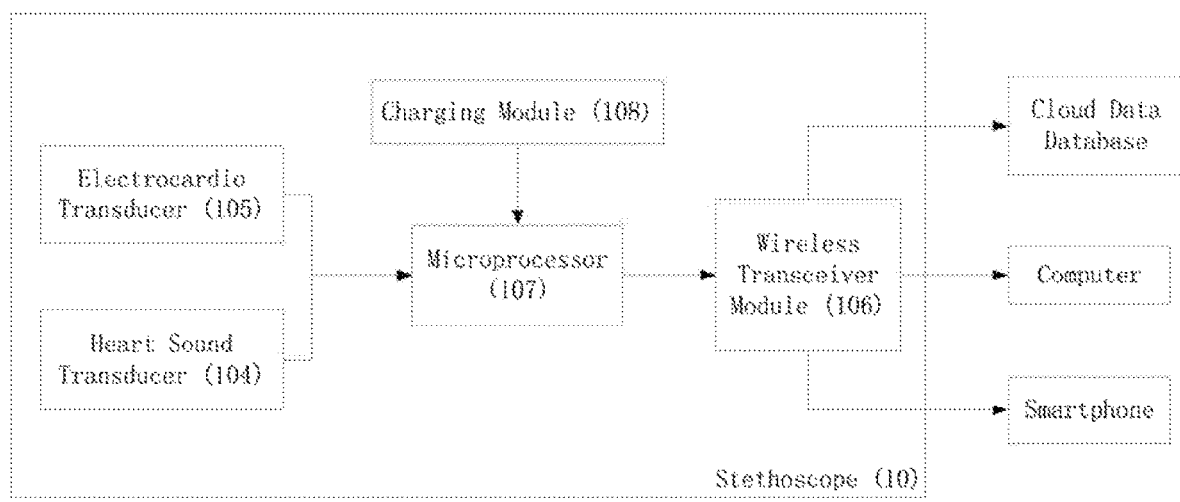

In a specific example, the signal synchronization device 100 may be, for example, an electronic chip integrated on a circuit board and be installed in the stethoscope 10, and may control a cooperative operation processing between other related electronic elements (e.g., the electrocardio transducer 105, the heart sound transducer 104) in the signal synchronization device 100 and the stethoscope 10 by a micro-controller 107 (as shown in FIG. 2E) on the circuit board.

In a preferred example, the stethoscope 10 further includes a wireless transceiver module 106, which may output the heart sound signal and the electrocardiographic signal, which are synchronous in time domain, output via the signal synchronization device 100 wirelessly. In an example, the wireless transceiver module 106 is, for example, a Bluetooth wireless transceiver module, and integrated on the circuit board within the stethoscope 10. However, the wireless transceiver module 106 is not limited thereto, but may also be other types of wireless transceiver module, such as Wi-Fi, ZigBee, customized wireless transceiver systems. Refer to FIG. 2E, in which the wireless transceiver module 106 may be in communicative connection with electronic equipments, such as cloud data database, computer or smartphone etc., and may transmit the electrocardiographic signal and the heart sound signal to the electronic equipments mentioned above wirelessly. However, the stethoscope 10 is not limited thereto, but may also be connected to a computer or a smartphone in a wired manner via data lines by using a data transmission interface (e.g., USB interface, HDMI interface), and perform transmission operation of the electrocardiographic signal and the heart sound signal.

Refer to FIG. 2E continuously. In another example, the stethoscope 10 also has a charging module 108 to provide a charging capability for the stethoscope 10. The charging module 108 may perform charging for the stethoscope 10 in, for example, a wireless charging or a wired charging manner.

Moreover, the circuit board of the stethoscope 10 further has an electrocardiographic signal processing circuit and a heart sound signal processing circuit integrated thereon, and performs analog to digital processing operation for the electrocardiographic signal and the heart sound signal separately by a control of the microprocessor 107.

Figure 2F:
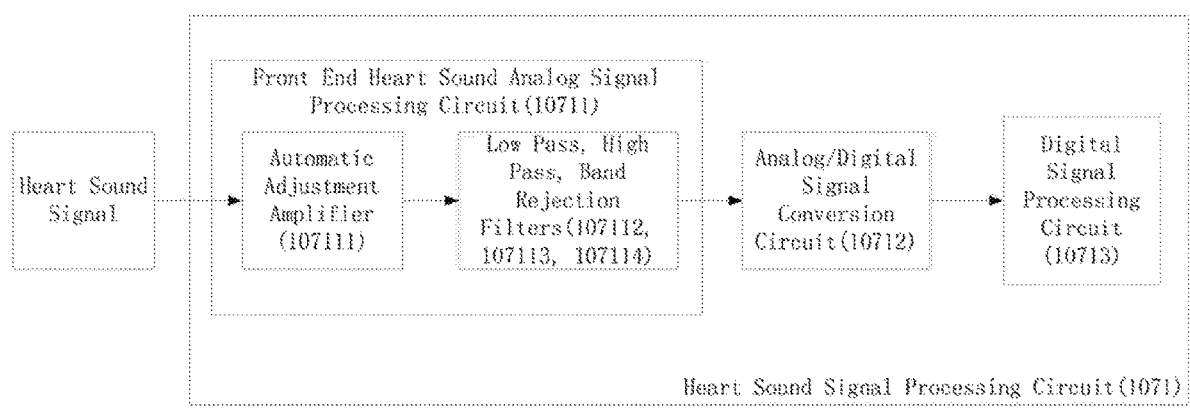

Refer to FIG. 2F in conjunction. The heart sound signal processing circuit 1071 includes a front end heart sound analog signal processing circuit 10711, an analog/digital signal conversion circuit 10712 and a digital signal processing circuit 10713. Wherein, the front end heart sound analog signal processing circuit 10711 further includes an automatic adjustment amplifier 107111 as well as low pass, high pass, band rejection filters 107112, 107113, 107114. The automatic adjustment amplifier 107111 is used to receive acquired heart sound signals, and may adjust required magnifying powers automatically according to strengths of the heart sound signals of different subjects to comply with signal voltages required by back end circuits. The low pass filter 107112, the high pass filter 107113 and the band rejection filter 107114 perform analog signal processing with specific cut-off frequencies separately to filter out noise other than the heart sound signals. The analog/digital signal conversion circuit 10712 is used to convert a heart sound analog signal into a heart sound digital signal, preserving integrity of original heart sound signals with a high resolution, low distortion design, being capable of providing subsequent digital signal processing. The digital signal processing circuit 10713 is a dynamically adjustable digital filter capable of filtering out movement noise generated due to movement of the stethoscope 10 when using the stethoscope 10, so that signal quality is maintained and digital signal processing required for signal feature extraction and feature classification can also be performed to provide artificial intelligence system or analysis module for signal identification and diagnosis.

Figure 2G:
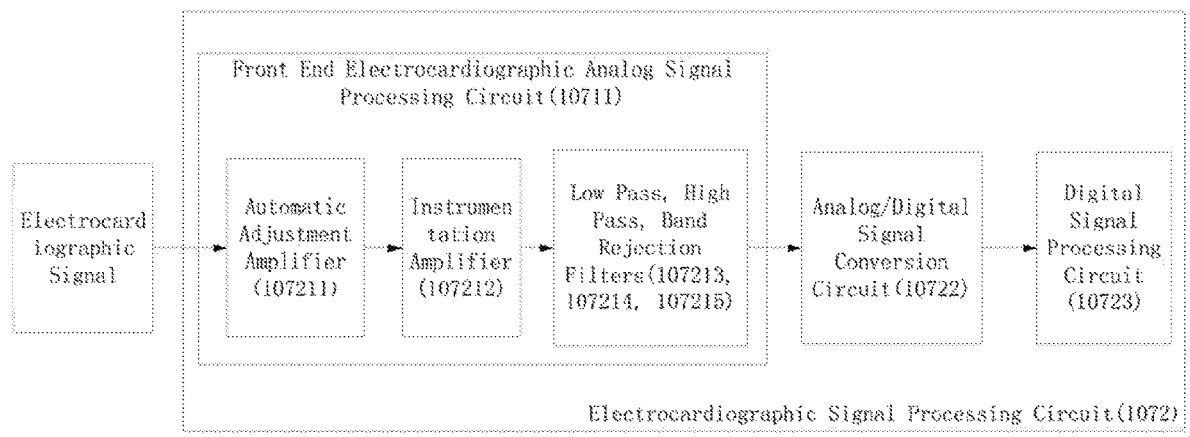

Refer to FIG. 2G in conjunction. The electrocardiographic signal processing circuit 1072 includes a front end electrocardiographic analog signal processing circuit 10721, an analog/digital signal conversion circuit 10722 and a digital signal processing circuit 10723. Wherein, the front end electrocardiographic analog signal processing circuit 10721 comprises an automatic adjustment amplifier 107211, an instrumentation amplifier 107212 as well as low pass, high pass and band rejection filters 107213, 107214, 107215. The automatic adjustment amplifier 107211 is used to receive acquired electrocardiographic signals, and may adjust required magnifying powers automatically according to strengths of the electrocardiographic signals of different subjects to comply with signal voltages required by back end circuits. The instrumentation amplifier 107212 is used to eliminate common mode noise, providing the electrocardiographic signals with lower noise for subsequent circuits to process. The low pass filter 107213, the high pass filter 107214 and the band rejection filter 107215 perform analog signal processing with specific cut-off frequencies separately, and may filter out noise other than the electrocardiographic signals. The analog/digital signal conversion circuit 10722 is used to convert a electrocardiographic analog signal into a electrocardiographic digital signal, preserving integrity of original electrocardiographic signals with a high resolution, low distortion design, being capable of providing subsequent digital signal processing. The digital signal processing circuit 10723 is a dynamically adjustable digital filter capable of filtering out movement noise generated due to operation and movement of the stethoscope 10 done by the user for maintaining signal quality and digital signal processing required for signal feature extraction and feature classification can also be performed to provide artificial intelligence system or analysis module for signal identification and diagnosis.

Figure 3:
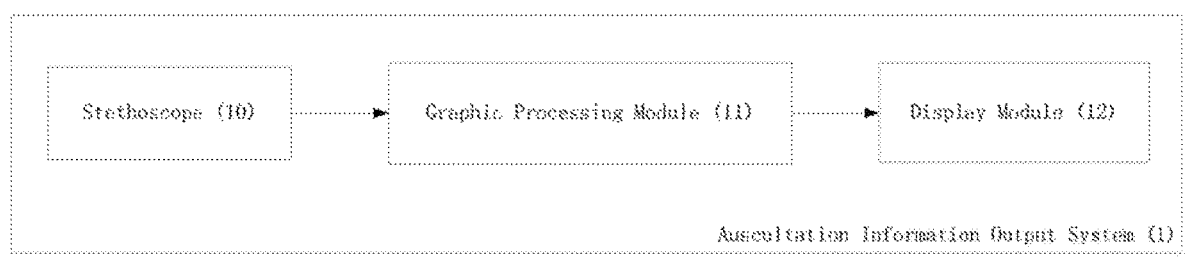
FIG. 3 is a schematic view showing a basic architecture of an auscultation information output system in a third implementation of the invention.

FIG. 3 is a schematic view showing a basic architecture of an auscultation information output system 1 in a third implementation of the invention. As shown in the figure, the auscultation information output system 1 of the invention mainly includes a stethoscope 10, a graphic processing module 11 and a display module 12.

The stethoscope 10 is used to acquire an electrocardiographic signal and a heart sound signal of a user, and perform synchronization for the electrocardiographic signal and the heart sound signal, as well as output the electrocardiographic and heart sound signals which are synchronous in time domain. Since a structure arrangement of the stethoscope 10 and a synchronization technical means thereof have been detailed in FIGS. 2A to 2C above, there is no redundant description here.

The graphic processing module 11 is used for patterning the heart sound signal and the electrocardiographic signal which are output by the stethoscope 10 and are synchronous in time domain to generate an electrocardio graphic information and a heart sound graphic information in correspondence.

The display module 12 is used for displaying the electrocardio graphic information and the heart sound graphic information.

In a practical application, the graphic processing module 11 and the display module 12 may be arranged in an electronic equipment, such as a personal computer, a tablet computer, a smartphone etc. The electronic equipment is in communicative connection (in a wired or wireless manner) with the stethoscope 10 to receive the electrocardiographic signal and the heart sound signal, which are output by the stethoscope 10 and are subject to patterning, followed by outputting an electrocardiogram and a cardiophonogram in correspondence.

Figure 4A:
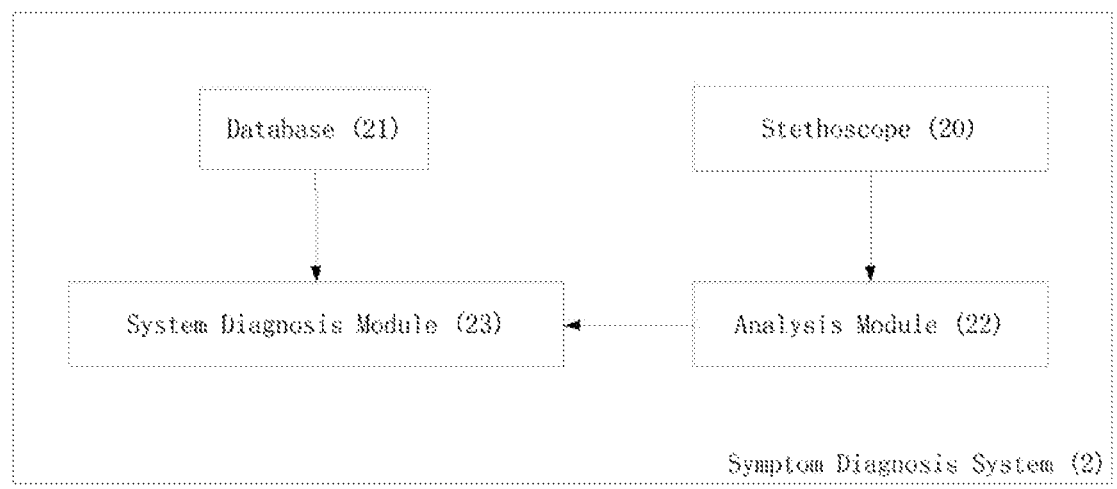
FIG. 4A is a schematic view showing a basic architecture of a symptom diagnosis system in a fourth implementation of the invention.

Refer to FIG. 4A in conjunction, which is a schematic view showing a basic architecture of a symptom diagnosis system 2 in a fourth implementation of the invention. As shown in FIG. 4A, the symptom diagnosis system 2 mainly includes a stethoscope 20, a database 21, an analysis module 22 and a system diagnosis module 23.

The database 21 is used for storing a heart sound symptom information and an electrocardiographic symptom information.

The stethoscope 20 is used to acquire an electrocardiographic signal and a heart sound signal of a user, and perform synchronization for the electrocardiographic signal and the heart sound signal, as well as output the electrocardiographic and heart sound signals which are synchronous in time domain. Since a structure arrangement of the stethoscope 20 and a synchronization technical means thereof are fundamentally identical to those of the stethoscope 10 illustrated in FIGS. 2A to 2G, there is no redundant description here.

The analysis module 22 is used for analyzing the heart sound signal and the electrocardiographic signal which are output by the stethoscope 10 and are synchronous in time domain to obtain a heart sound characteristic included in the heart sound signal, and obtain an electrocardiographic characteristic included in the electrocardiographic signal. In a preferred example, the database 21 further stores heart sound signals and electrocardiographic signals of normal human bodies therein.

The analysis module 22 determines whether or not the electrocardiographic signal and the heart sound signal output by the stethoscope 10 are matched according to the heart sound signals and the electrocardiographic signals of the normal human bodies stored in the database 21. In case of matching, the electrocardiographic signal and the heart sound signal of the user are both normal. In case of mismatching, the electrocardiographic signal or the heart sound signal of the user is abnormal, and the heart sound characteristic and the electrocardiographic characteristic which represent anomaly are extracted from the electrocardiographic signal or the heart sound signal for subsequent further symptom analysis of the heart sound characteristic and the electrocardiographic characteristic.

The system diagnosis module 23 performs analyzes for the heart sound characteristic and the electrocardiographic characteristic obtained by the analysis module 22 according to the heart sound symptom information and the electrocardiographic symptom information stored in the database 21. As the heart sound characteristic is matched with the heart sound symptom information stored in the database 21 through analysis, a heart sound system diagnosis result comprising the heart sound symptom information is output. Alternatively, as the electrocardiographic characteristic is matched with the electrocardiographic symptom information stored in the database 21 through analysis, an electrocardiographic system diagnosis result comprising the electrocardiographic symptom information is output. That is, according to the heart sound characteristic and the electrocardiographic symptom information, which represent anomaly, extracted by the analysis module 22, the system diagnosis module 23 inquires a symptom information, which is matched therewith, from the database 21, and outputs a diagnosis result for users without medical profession to reference and to know immediately whether or not they suffer from cardiovascular diseases accordingly. The acquired heart sound and electrocardiographic signals have undergone synchronous calibration processing, so that diagnosis effectiveness of the symptom diagnosis system for cardiovascular diseases may be improved.

Figure 4B:
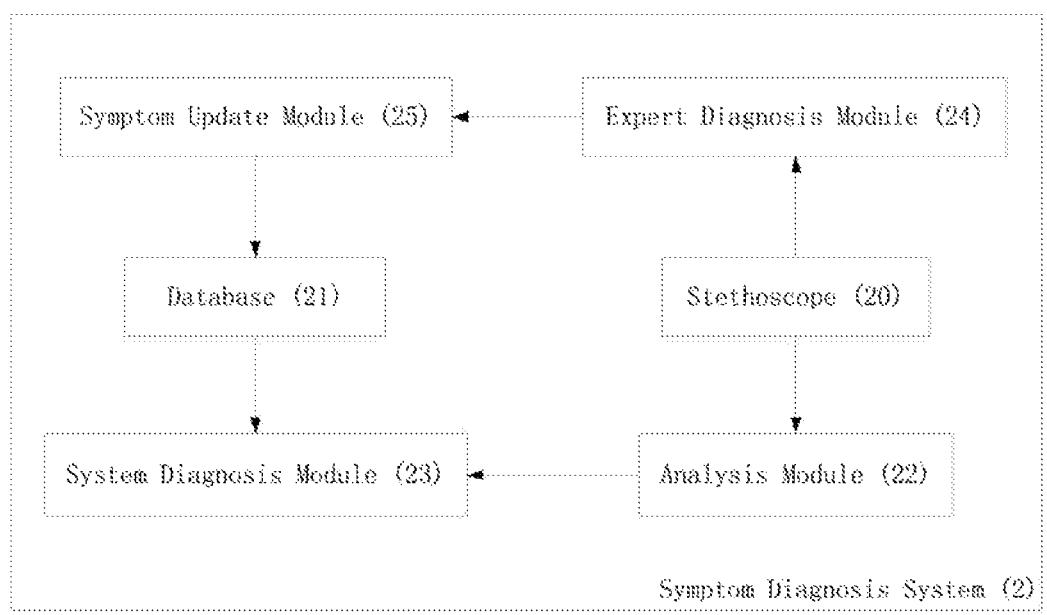
FIGS. 4B-4C are schematic views showing different examples of the symptom diagnosis system shown in FIG. 4A.

Refer to FIG. 4B in conjunction. Since diagnosis processes of cardiovascular diseases are more complex, in an example of the invention, the symptom diagnosis system 2 further includes an expert diagnosis module 24 and a symptom update module 25, wherein the expert diagnosis module 24 allows an expert to perform diagnosis for the electrocardiographic signal and the heart sound signal output by the stethoscope 10 manually, and outputs a heart sound expert diagnosis result and an electrocardiographic expert diagnosis result. Moreover, the symptom update module 25 is used to correct/update the heart sound symptom information stored in the database 21 according to the heart sound expert diagnosis result as the heart sound system diagnosis result and the heart sound expert diagnosis result are mismatched, and correct/update the electrocardiographic symptom information stored in the database 21 according to the electrocardiographic expert diagnosis result as the electrocardiographic system diagnosis result and the electrocardiographic expert diagnosis result are mismatched. By means of such mechanism, when the system diagnosis module 23 cannot perform determination for the electrocardiographic characteristic or the heart sound characteristic according to existing information in the database 21, or alternatively when anomaly exists in a system diagnosis result output by the system diagnosis module 23 for the electrocardiographic characteristic or the heart sound characteristic according to existing information in the database 21, the expert diagnosis module 24 may allow related medical professionals to perform human intervention for aiding in diagnosis of symptom, and the database 21 is allowed to update the heart sound symptom information provided from related medical professionals and the electrocardiographic symptom information stored therein constantly for increasing accuracy of the diagnosis result of the system diagnosis module 23.

Moreover, with the arrangement mentioned above, the symptom diagnosis system 2 of the invention may also be used for the purpose of education. That is, the electrocardiographic signal and the heart sound signal with existent anomaly are output by the expert diagnosis module 24 for related learners to determine related symptoms, and are further compared with the system diagnosis result output by the system diagnosis module 23 to determine whether or not the determination result of the learner is matched with the system diagnosis result. Thereby, the purpose of education is achieved.

Figure 4C:
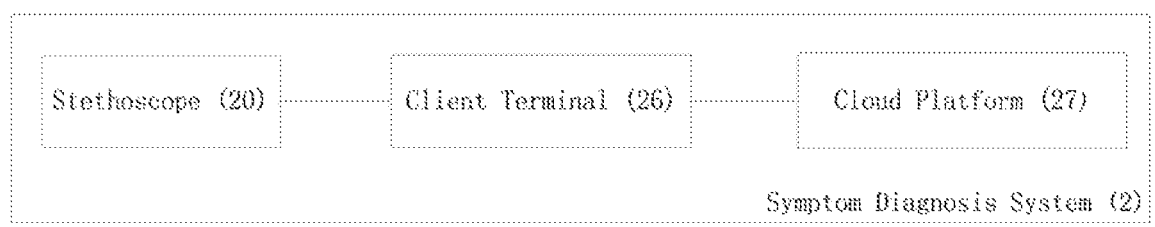

Refer to FIG. 4C continuously. In another example of the invention, the symptom diagnosis system 2 further includes a stethoscope 20, a client terminal 26 and a cloud platform 27, wherein a structure arrangement of the stethoscope 20 and a synchronization technical means thereof are fundamentally identical to those of the stethoscope 10 illustrated in FIGS. 2A to 2G, while the only difference is that the stethoscope 20 may further provide a stethoscope binding instruction and a stethoscope unbinding instruction. The client terminal 26 is used to provide a binding instruction of client terminal and an unbinding instruction of client terminal.

For the use of the cloud platform 27, the cloud platform 27 may create a binding relationship between the stethoscope 20 and the client terminal 26 on one end thereof only when the stethoscope binding instruction provided by the stethoscope 20 and the binding instruction of client terminal provided by the client terminal 26 are received simultaneously so that the client terminal 26 may receive the heart sound signal and the electrocardiographic signal, which are synchronous in time domain, output by the stethoscope 20. Alternatively, the cloud platform 27 may relieve the binding relationship between the stethoscope 20 and the client terminal 26 only when the stethoscope unbinding instruction provided by the stethoscope 20 and the unbinding instruction of client terminal provide by the client terminal 26 are received simultaneously. From the above, through the bidirectional pair confirmation mechanism mentioned above, the stethoscope 20 and the client terminal 26 may be allowed to perform pairing or unpairing operation only when both of them send confirmation messages for pairing or unpairing according to the invention. Moreover, in a general situation, the stethoscope 20 is limited to perform pairing with the client terminal 26 only in the same time of use according to the invention. Thereby, the stethoscope 20 is prevented from data leak issues effectively to ensure privacy security of users accordingly.

Whereby, the signal synchronization device of the invention generates a mixed time domain information by receiving an electrocardiographic signal and a heart sound signal synchronously, and performs time domain and frequency domain transformations for the mixed time domain information to obtain an electrocardiographic signal calibration factor and a heart sound signal calibration factor separately, in order to perform calibrations for the electrocardiographic signal and the heart sound signal according thereto separately, so that the output electrocardiographic and heart sound signals are synchronous in time domain. Thereby, necessary references are provided for early diagnosis of cardiovascular diseases by applying the signal synchronization device mentioned above in the stethoscope, the auscultation information output system and the symptom diagnosis system.

Furthermore, by providing the expert diagnosis module, the symptom diagnosis system of the invention may update the symptom information in the database according to a diagnosis result of an expert as the diagnosis results of the expert and the diagnosis system are inconsistent for the heart sound signal and the electrocardiographic signal. Thereby, the accuracy for the diagnosis result of the symptom diagnosis system may be increased effectively.

In addition, the symptom diagnosis system of the invention provides a bidirectional pair confirmation mechanism for the stethoscope and the client terminal, and unifies management of the binding and unbinding operations between the stethoscope and the client terminal. Thereby, it may ensures effectively that the sensed data acquired by the stethoscope are insusceptible to leak, so that the privacy security of user of the stethoscope is protected.

The examples above are only illustrative to explain principles and effects of the invention, but not to limit the invention. It will be apparent to those skilled in the art that modifications and variations can be made without departing from the spirit and scope of the invention. Therefore, the protection range of the rights of the invention should be as defined by the appended claims.

What is claimed is:

1. A stethoscope using a signal synchronization device for auscultating a user, the stethoscope including:
   a pickup member for collecting a heart sound signal of the user;
   a sound guiding pipe for conducting a heart sound signal;
   a slave member sheathing the pickup member for contacting the user due to a motion of the pickup member;
   a heart sound transducer arranged on the sound guiding pipe, the heart sound transducer having a heart sound transduction portion, which is oriented to the pickup member for acquiring the heart sound signal;
   an electrocardio transducer arranged on the slave member, the heart sound transducer having an electrocardio transduction portion, which is exposed to a portion of the slave member contacting the user for acquiring the electrocardiographic signal;
   wherein the signal synchronization device is used to perform synchronous calibration for the electrocardiographic signal and the heart sound signal on the stethoscope, the signal synchronization device including:
   a signal receiving module for receiving the electrocardiographic signal acquired by the electrocardiographic signal transducer and the heart sound signal acquired by the heart sound transducer separately to generate a first electrocardiographic time domain information and a first heart sound time domain information separately, the first electrocardiographic time domain information comprising a first electrocardio generation time point of the electrocardiographic signal, the first heart sound time domain information comprising a first heart sound generation time point of the heart sound signal;
   a synchronization factor generation module for receiving the electrocardiographic signal and the heart sound signal synchronously to generate a mixed time domain information, and performing time domain and frequency domain transformations for the mixed time domain information to obtain a second electrocardiographic time domain information representing the electrocardiographic signal in the mixed time domain information, the second electrocardiographic time domain information comprising a second electrocardio generation time point of the electrocardiographic signal, and to obtain a second heart sound time domain information representing the heart sound signal in the mixed time domain information, the second heart sound time domain information comprising a second heart sound generation time point of the heart sound signal, and allowing the second electrocardio generation time point and the second heart sound generation time point to be synchronous in time domain by using the second electrocardiographic time domain information as an electrocardiographic signal calibration factor, and using the second heart sound time domain information as a heart sound signal calibration factor, wherein the time domain synchronization is performed by adjusting time axis; and
   a synchronization module used to calibrate the electrocardiographic signal and the heart sound signal received by the signal receiving module at least once by adjusting time axis according to the electrocardiographic signal synchronization factor and the heart sound signal synchronization factor separately for keeping the first electrocardio generation time point and the second electrocardio generation time point consistent, and for keeping the first heart sound generation time point and the second heart sound generation time point consistent, such that the electrocardiographic signal and the heart sound signal received by the signal receiving module are synchronous in time domain.

2. The signal synchronization device according to claim 1, wherein the synchronization factor generation module performs a time domain to frequency domain transformation for the mixed time domain information to generate a mixed frequency domain information, followed by acquiring a main frequency characteristic in the mixed frequency domain information, and defining a heart sound frequency domain information representing the heart sound signal and defining an electrocardiographic frequency domain information representing the electrocardiographic signal from the mixed frequency domain information according to the main frequency characteristic, followed by performing a frequency domain to time domain transformation for the mixed frequency domain information to generate the mixed time domain information, in order to define the second heart sound time domain information in the mixed time domain signal by the heart sound frequency domain information and define the second electrocardiographic time domain information in the mixed time domain signal by the electrocardiographic frequency domain information.

3. The stethoscope according to claim 1, further including:
   a wireless transceiver module outputting the heart sound signal and the electrocardiographic signal, which are synchronous in time domain, wirelessly.

4. The stethoscope according to claim 3, wherein the wireless transceiver module is a Bluetooth transceiver module, a Wi-Fi module, a ZigBee transceiver module, or any customized wireless transceiver module.

5. An auscultation information output system, using the stethoscope according to claim 1, the auscultation information output system including:
- a graphic processing module for patterning the heart sound signal and the electrocardiographic signal synchronized by the stethoscope in time domain to generate an electrocardio graphic information and a heart sound graphic information; and
- a display module for displaying the electrocardio graphic information and the heart sound graphic information.

6. A symptom diagnosis system, using the stethoscope according to claim 1, the symptom diagnosis system including:
- a database for storing a heart sound symptom information and an electrocardiographic symptom information;
- an analysis module for analyzing the heart sound signal and the electrocardiographic signal synchronized by the stethoscope in time domain to obtain a heart sound characteristic included in the heart sound signal, and obtain an electrocardiographic characteristic included in the electrocardiographic signal; and
- a system diagnosis module, which outputs a heart sound system diagnosis result comprising the heart sound symptom information as the heart sound characteristic and the heart sound symptom information are matched; outputs an electrocardiographic system diagnosis result comprising the electrocardiographic symptom information as the electrocardiographic characteristic and the electrocardiographic symptom information are matched.

7. The symptom diagnosis system according to claim 6, further including:
- an expert diagnosis module, which diagnoses the heart sound signal and outputs a heart sound expert diagnosis result, and diagnoses the electrocardiographic signal and outputs an electrocardiographic expert diagnosis result; and
- a symptom update module, which corrects/updates the heart sound symptom information of the database according to the heart sound expert diagnosis result as the heart sound system diagnosis result and the heart sound expert diagnosis result are mismatched; corrects/updates the electrocardiographic symptom information of the database according to the electrocardiographic expert diagnosis result as the electrocardiographic system diagnosis result and the electrocardiographic expert diagnosis result are mismatched.

8. The symptom diagnosis system according to claim 6, wherein the stethoscope capable of providing a stethoscope binding instruction and a stethoscope unbinding instruction, the symptom diagnosis system further including:
- a client terminal, which provides a client terminal binding instruction and client terminal unbinding instruction; and
- a cloud platform, which can create a binding relationship of the stethoscope and the client terminal only when the stethoscope binding instruction and the client terminal binding instruction are received simultaneously so that the client terminal can receive the heart sound signal and the electrocardiographic signal synchronized by the stethoscope in time domain, or relieve the binding relationship of the stethoscope and the client terminal only when the stethoscope unbinding instruction and the client terminal unbinding instruction are received simultaneously.

* * * * *